US009092762B2

(12) United States Patent  
Jensen et al.

(10) Patent No.: US 9,092,762 B2  
(45) Date of Patent: Jul. 28, 2015

(54) MEDICAL DEVICE MAINTENANCE SYSTEM

(75) Inventors: Eric P. Jensen, Niskayuna, NY (US); Jason Paul DiFraia, Auburn, NY (US); Michael Allan Ehrhart, Liverpool, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 138 days.

(21) Appl. No.: 13/440,571

(22) Filed: Apr. 5, 2012

(65) Prior Publication Data

US 2013/0268890 A1 Oct. 10, 2013

(51) Int. Cl.
*G06F 3/048* (2013.01)
*G06Q 10/00* (2012.01)
*G06F 19/00* (2011.01)

(52) U.S. Cl.
CPC .............. *G06Q 10/20* (2013.01); *G06F 19/327* (2013.01); *G06F 19/3412* (2013.01)

(58) Field of Classification Search
USPC ......................................... 715/825, 764, 771
See application file for complete search history.

(56) References Cited

U.S. PATENT DOCUMENTS

| 8,402,161 | B2 | 3/2013 | DelloStritto et al. | |
|---|---|---|---|---|
| 2003/0182014 | A1* | 9/2003 | McDonnell et al. | 700/159 |
| 2005/0137653 | A1 | 6/2005 | Friedman et al. | |
| 2009/0005927 | A1* | 1/2009 | Schlatre et al. | 701/30 |
| 2009/0099867 | A1* | 4/2009 | Newman | 705/2 |
| 2009/0182594 | A1* | 7/2009 | Choubey | 705/7 |
| 2010/0076809 | A1* | 3/2010 | Eryurek et al. | 705/9 |
| 2010/0131084 | A1* | 5/2010 | Van Camp | 700/86 |
| 2010/0287006 | A1* | 11/2010 | Cannon et al. | 705/3 |
| 2011/0071420 | A1 | 3/2011 | St. Pierre et al. | |
| 2012/0095926 | A1* | 4/2012 | Nishimura et al. | 705/301 |
| 2012/0299727 | A1* | 11/2012 | Newman et al. | 340/540 |

FOREIGN PATENT DOCUMENTS

| JP | 2006149873 A | 6/2006 |
|---|---|---|
| JP | 2011175575 A | 9/2011 |
| JP | 2011204205 A | 10/2011 |

OTHER PUBLICATIONS

Rahul Nair et al., Fleet Management for Vehicle Sharing Operations, Nov. 2011, Journal Transportation Science, vol. 45 Issue 4, pp. 524-540.*

International Search Report & Written Opinion in PCT/US2013/031218 mailed Jun. 20, 2013, 11 pages.

* cited by examiner

*Primary Examiner* — Dennis Chow
*Assistant Examiner* — Tam Tran
(74) *Attorney, Agent, or Firm* — Merchant & Gould P.C.

(57) ABSTRACT

A system for maintaining medical devices includes: a computing device including memory and a processor that, when executing instructions stored on the memory, creates a user interface including: a health module providing a summary of a maintenance status of the medical devices; a location module providing a summary of a location of the medical devices; and a maintenance alert module providing a list of the medical devices needing maintenance, the list including a type of maintenance needed for each of the medical devices in the list.

8 Claims, 14 Drawing Sheets

MEDICAL DEVICE MAINTENANCE SYSTEM

BACKGROUND

Medical devices collect, monitor, and display various aspects associated with a patient's physiology. These medical devices need to be serviced at periodic intervals. For example, sensors, probes and similar devices on the medical devices may have a defined useful life (e.g., 6000 usage cycles) before those devices must be replaced. Likewise, the software and firmware running on the medical devices may need to be periodically updated.

SUMMARY

In one aspect, a system for maintaining medical devices includes: a computing device including memory and a processor that, when executing instructions stored on the memory, creates a user interface including: a health module providing a summary of a maintenance status of the medical devices; a location module providing a summary of a location of the medical devices; and a maintenance alert module providing a list of the medical devices needing maintenance, the list including a type of maintenance needed for each of the medical devices in the list.

In another aspect, a method for providing maintenance information for a plurality of medical devices includes: receiving maintenance information from the medical devices; providing a summary of the maintenance information, the summary including: a summary of a maintenance status of the medical devices; a summary of a location of the medical devices; and a list of the medical devices needing maintenance, the list including a type of maintenance needed for each of the medical devices in the list; and providing access to the summary of the maintenance information outside a network associated with the medical devices.

In yet another aspect, a computer-readable storage medium encodes instructions that, when executed by a processor, cause the processor to perform steps including: receiving maintenance information from the medical devices; providing a summary of the maintenance information, the summary including: a summary of a maintenance status of the medical devices; a summary of a location of the medical devices; a list of the medical devices needing maintenance, the list including a type of maintenance needed for each of the medical devices in the list; a summary of a state of connection of the medical devices; and a summary of firmware and software updates for the medical devices; filtering the list of the medical devices based on device or location; allowing a user to approve the firmware or software upgrade to be applied one or more of the medical devices on the list; notifying the medical devices to update the firmware or software; receiving an indication that maintenance for a given medical device has been performed; and removing the given medical device from the list.

DETAILED DESCRIPTION

The present disclosure relates to maintaining medical devices. In example embodiments, the medical devices can be spread throughout a facility, such as a clinic or hospital. In other examples, the medical devices can be spread across multiple facilities. The system collects maintenance information associated with the medical devices, such as usage and configuration information. The system allows a technician to review the status of the medical devices and to make decisions on the maintenance of the medical devices.

Figure 1:
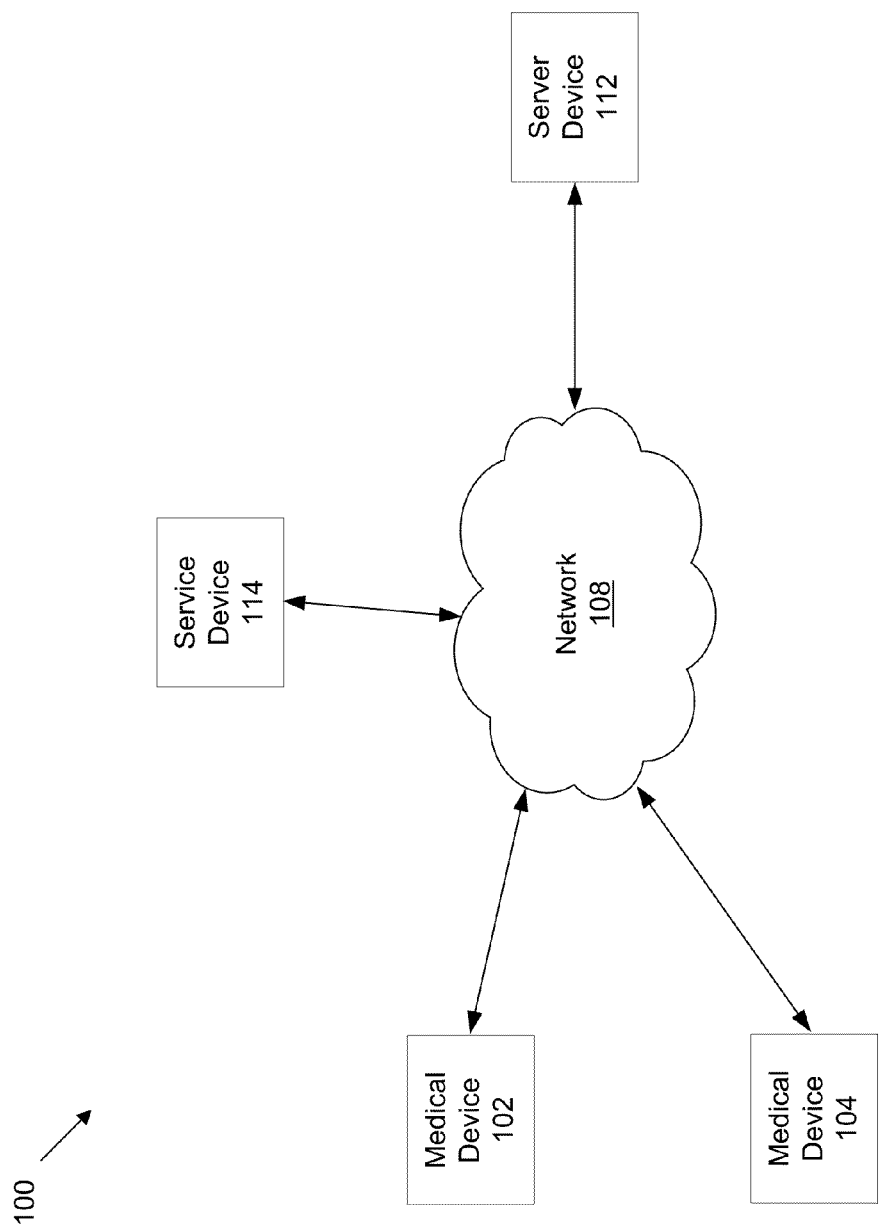
FIG. 1 shows an example system for maintaining medical devices.

FIG. 1 is a block diagram illustrating an example system 100 for medical devices.

In this example, medical devices 102, 104 are used to collect physiological data from patients. These medical devices can be located in a facility, such as a hospital or clinic. In one example, the devices 102, 104 are located at the same facility. In another example, the devices are located at different facilities spread out geographically.

The medical devices 102, 104 communicate with a network 108. In one example, the medical devices 102, 104 and the network 108 are part of a CONNEX™ system from Welch Allyn of Skaneateles Falls, N.Y., although other systems can be used. In such an example, the medical devices communicate through known protocols, such as the Welch Allyn Communications Protocol (WACP). WACP uses a taxonomy as a mechanism to define information and messaging. Taxonomy can be defined as description, identification, and classification of a semantic model. Taxonomy as applied to a classification scheme may be extensible. Semantic class-based modeling utilizing taxonomy can minimize the complexity of data description management by limiting, categorizing, and logically grouping information management and operational functions into families that contain both static and dynamic elements.

The network 108 is an electronic communication network that facilitates communication between the medical devices 102, 104. An electronic communication network is a set of computing devices and links between the computing devices. The computing devices in the network use the links to enable communication among the computing devices in the network. The network 108 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the network 108 includes various types of links. For example, the network 108 can include wired and/or wireless links. Furthermore, in various embodiments, the network 108 is implemented at various scales. For example, the network 108 can be implemented as one or more local area networks (LANs), metropolitan area networks, subnets, wide area networks (such as the Internet), or can be implemented at another scale.

In this example, the medical devices 102, 104 and the network 108 are all part of the same network. In other words, the medical devices 102, 104 and the network 108 communicate with one another over a LAN behind a wall safeguarding the devices from outside influences on the Internet, such as a firewall.

The medical devices 102, 104 can provide various types of functionality. For example, the set of medical devices 102, 104 can include one or more physiological monitor devices (such as the medical device 102). In addition, the medical devices 102, 104 can include one or more desktop, laptop, or wall-mounted devices. In addition, the medical devices 102, 104 can include one or more physiological monitor devices. Such monitor devices can display representations of physiological parameters. A monitor device could, for example, be used by a clinician to monitor the physiological parameters of multiple patients at one time. Such monitor devices are typically not wall mounted.

The medical devices 102, 104 can communicate with each other through the network 108. In various embodiments, the medical devices 102, 104 can communicate various types of data with each other through the network 108. For example, in embodiments where the medical devices 102, 104 includes a set of physiological monitor devices and a monitor device, each of the physiological monitor devices can send data representing measurements of physiological parameters of patients to the monitor device. In this way, the medical devices 102, 104 can display representations of physiological parameters to a clinician.

The medical devices 102, 104 can send various types of data and can receive various types of data through the network 108. For example, in some embodiments, the medical devices 102, 104 can send measurements of physiological parameters. In another example, the medical devices 102, 104 can retrieve past measurements of physiological parameters of patients.

A server device 112 communicates through the network 108 with the medical devices 102, 104. In this example, the server device 112 monitors the status of the medical devices 102, 104 to determine various attributes of the medical devices 102, 104, such as maintenance requirements and upgrade requirements.

In this example, the server device 112 is located "in the cloud." In other words, the server device 112 is located outside of the internal network associated with the medical devices 102, 104. Typically, the server device 112 does not communicate directly with the medical devices 102, 104, but instead communicates with a central server located within the same network as the medical devices 102, 104, such as the CONNEX™ system from Welch Allyn of Skaneateles Falls, N.Y. Intermediary servers in the CONNEX™ system, in turn, communicate with the medical devices 102, 104. Other configurations are possible.

The medical devices 102, 104 and the server device 112 are computing devices. As used herein, a computing system is a system of one or more computing devices. A computing device is a physical, tangible device that processes data. Example types of computing devices include personal computers, standalone server computers, blade server computers, mainframe computers, handheld computers, smart phones, special purpose computing devices, and other types of devices that process data.

Figure 2:
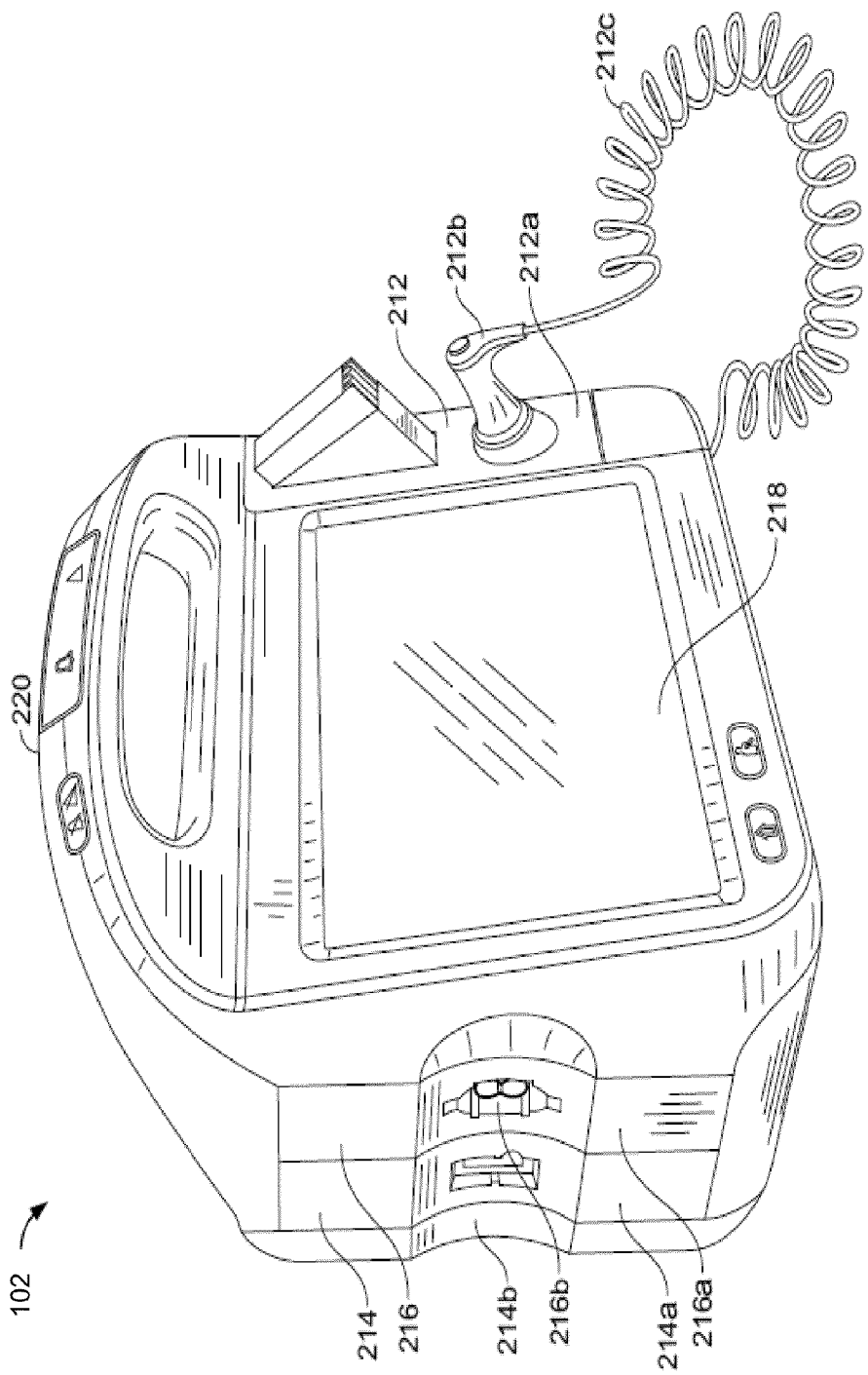
FIG. 2 shows an example medical device of the system of FIG. 1.

FIG. 2 illustrates one example of the medical device 102. The medical device 102 is portable. The medical device 102 includes multiple health care equipment (HCE) modules. Each of the HCE modules is configured to measure one or more physiological parameters of a health-care recipient, also referred to herein as a patient.

A temperature measurement module 212 is accessible from the front side of the medical device 102. A SpO2 module 214 and a non-invasive blood pressure (NIBP) module 216 are accessible from a left hand side of the medical device 102. An upper handle portion 220 enables the medical device 102 to be carried by hand.

A front side of the medical device 102 includes a display screen 218 and an outer surface of the temperature measurement module 212. The temperature measurement module 212 is designed to measure the body temperature of a patient. As used in this document, a "module" is a combination of a physical module structure which typically resides within the medical device 102 and optional peripheral components (not shown) that typically attach to and reside outside of the medical device 102.

The temperature measurement module 212 includes a front panel 212a. The front panel 212a has an outer surface that is accessible from the front side of the medical device 102. The front panel 212a provides access to a wall (not shown) storing a removable probe (not shown), also referred to as a temperature probe, that is attached to a probe handle 212b. The probe and its attached probe handle 212b are tethered to the temperature measurement module 212 via an insulated conductor 212c. The probe is designed to make physical contact with a patient in order to sense a body temperature of the patient.

A left hand side of the medical device 102 includes an outer surface of the SpO2 module 214 and an outer surface of the NIBP module 216. The SpO2 module 214 is a HCE module designed to measure oxygen content within the blood of a patient. The NIBP module 216 is a HCE module designed to measure blood pressure of a patient.

As shown, the SpO2 module 214 includes a front panel 214a. The front panel 214a includes an outer surface that is accessible from the left side of the medical device 102. The front panel 214a includes a connector 214b that enables a connection between one or more peripheral SpO2 components (not shown) and a portion of the SpO2 module 214 residing inside the medical device 102. The peripheral SpO2 components reside external to the medical device 102. The peripheral SpO2 components are configured to interoperate with the SpO2 module 214 when connected to the SpO2 module 214 via the connector 214b. In some embodiments, the peripheral SpO2 components include a clip that attaches to an appendage of a patient, such as a finger. The clip is designed to detect and measure a pulse and an oxygen content of blood flowing within the patient.

As shown, the NIBP module 216 includes a front panel 216a having an outer surface that is accessible from the left side of the medical device 102. The front panel 216a includes a connector 216b that enables a connection between one or more peripheral NIBP components (not shown) and a portion of the NIBP module 216 residing inside the medical device 102. The peripheral NIBP components reside external to the medical device 102. The peripheral NIBP components are configured to interoperate with the NIBP module 216 when connected to the NIBP module 216 via the connector 216b. In some embodiments, the peripheral NIBP components include an inflatable cuff that attaches to an appendage of a patient, such as an upper arm of the patient. The inflatable cuff is designed to measure the systolic and diastolic blood pressure of the patient, the mean arterial pressure (MAP) of the patient, and the pulse rate of blood flowing within the patient.

The medical device 102 is able to operate within one or more workflows. A workflow is a series of one or more tasks that a user of the medical device 102 performs. When the medical device 102 operates within a workflow, the medical device 102 provides functionality suitable for assisting the user in performing the workflow. When the medical device 102 operates within different workflows, the medical device 102 provides different functionality.

When the medical device 102 is manufactured, the medical device 102 is configured to be able to operate within one or more workflows. After the medical device 102 is manufactured, the medical device 102 can be reconfigured to operate within one or more additional workflows. In this way, a user can adapt the medical device 102 for use in different workflows as needed.

In various embodiments, the medical device 102 operates within various workflows. For example, in some embodiments, the medical device 102 can operate within a monitoring workflow or a non-monitoring workflow. Example types of non-monitoring workflows include, but are not limited to, a spot check workflow and a triage workflow.

In example embodiments, the names for the workflows can be defined by the user. For example, the user can rename a "triage workflow" as "ED 3 North" or any other nomenclature as desired to provide more context to the user.

When the medical device 102 is operating within the monitoring workflow, the medical device 102 obtains a series of measurements of one or more physiological parameters of a single monitored patient over a period of time. In addition, the medical device 102 displays, on the display screen 218, a monitoring workflow home screen. The monitoring workflow home screen contains a representation of a physiological parameter of the monitored patient. The representation is based on at least one measurement in the series of measurements. A representation of a physiological parameter is a visible image conveying information about the physiological parameter.

For example, when the medical device 102 is operating within the monitoring workflow, the medical device 102 can obtain a blood pressure measurement of a single patient once every ten minutes for six hours. In this example, the medical device 102 displays a monitoring workflow home screen that contains a representation of the patient's blood pressure based on a most recent one of the temperature measurements. In this way, a user of the medical device 102 can monitor the status of the patient.

When the medical device 102 is operating within a non-monitoring workflow, the medical device 102 obtains a measurement of one or more physiological parameters from each patient in a series of patients. In addition, the medical device 102 displays a non-monitoring workflow home screen on the display screen 218. The non-monitoring workflow home screen contains a representation of the physiological parameter of a given patient in the series of patients. The representation is based on the measurement of the physiological parameter of the given patient.

In one example, when the medical device 102 is operating within a spot check workflow, the medical device 102 obtains blood pressure measurements from a series of previously-identified patients. In this other example, the medical device 102 displays a spot check workflow home screen containing a blood pressure measurement of a given patient in the series of previously-identified patients. In this way, a user of the medical device 102 can perform spot checks on the blood pressures of patients who have already been admitted to a hospital.

As used in this document, a patient is a previously identified patient when the medical device 102 stores information regarding the identity of the patient. In another example, when the medical device 102 is operating within a triage workflow, the medical device 102 can obtain a single blood pressure measurement from each patient in a series of unidentified patients as the patients arrive at a hospital. In this example, the medical device 102 displays a triage workflow home screen containing a representation of the patients' blood pressure based on the single blood pressure measurements of the patients. In this way, a user of the medical device 102 can perform triage on the series of unidentified patients as they arrive. As used in this document, a patient is an unidentified patient when the medical device 102 does not store information regarding the identity of the patient.

The monitoring workflow home screen is different than the non-monitoring workflow home screen. Further, as discussed below, the navigation options associated with the different workflows allows for efficient monitoring based on the environment in which the device is used. In various embodiments, the monitoring workflow home screen is different than the non-monitoring workflow home screen in various ways. For example, in some embodiments, the monitoring workflow home screen includes at least one user-selectable control that is not included in the non-monitoring workflow home screen. In other embodiments, a representation of a physiological parameter in the monitoring workflow home screen has a different size than a representation of the same physiological parameter in the non-monitoring workflow home screen.

Figure 3:
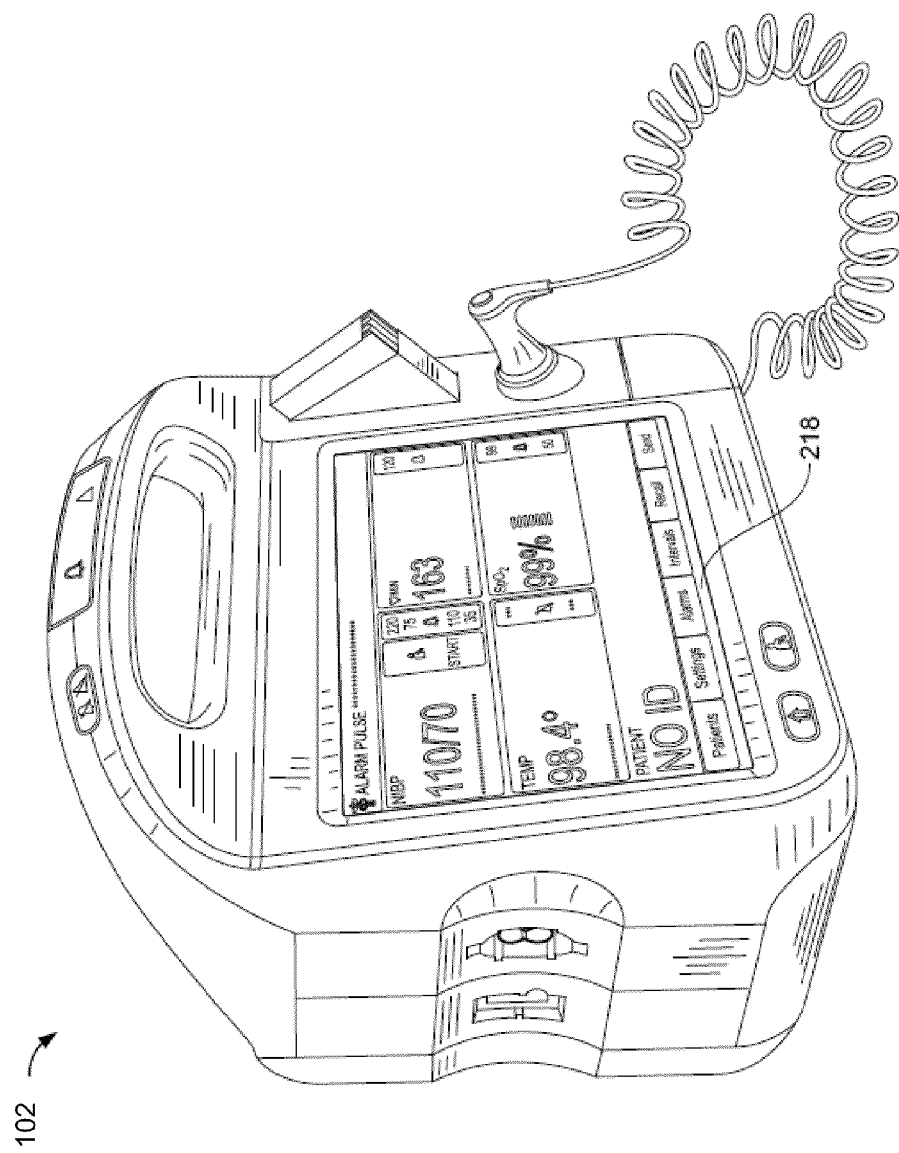
FIG. 3 shows another view of the medical device of FIG. 2.

FIG. 3 illustrates an example user interface displayed on the display screen 218 of FIG. 2. The medical device 102 outputs and displays user interfaces discussed in this document on the display screen 218.

In some examples described herein, the physiological monitor device is a portable device. In other examples, the physiological monitor device is a non-portable device, such as a computing device like a workstation. Many configurations are possible.

The medical device 102 shown in FIGS. 2-3 is only one example of a medical device. All different types of medical devices used to collect patient data can be used.

Referring again to FIG. 1, the medical devices 102, 104 send various data to and receive data. For example, as described above, the medical devices 102, 104 send physiological parameters associated with patients to various devices within the system 100 for consumption and storage.

In addition, the medical devices 102, 104 send maintenance information (e.g., configuration and usage information) to the server device 112. This maintenance information can be used to determine a current state of the medical devices 102, 104. The information can also be used to manage maintenance and upgrading of the medical devices 102, 104. For example, as described further below, the medical devices 102, 104 report usage information and current firmware/software configurations to the server device 112.

A service device 114 can be used by a technician to access the maintenance information stored on the server device 112. In one example, the service device 114 is a computing device that uses a browser to access the information associated with the medical devices 102, 104.

Figure 4:
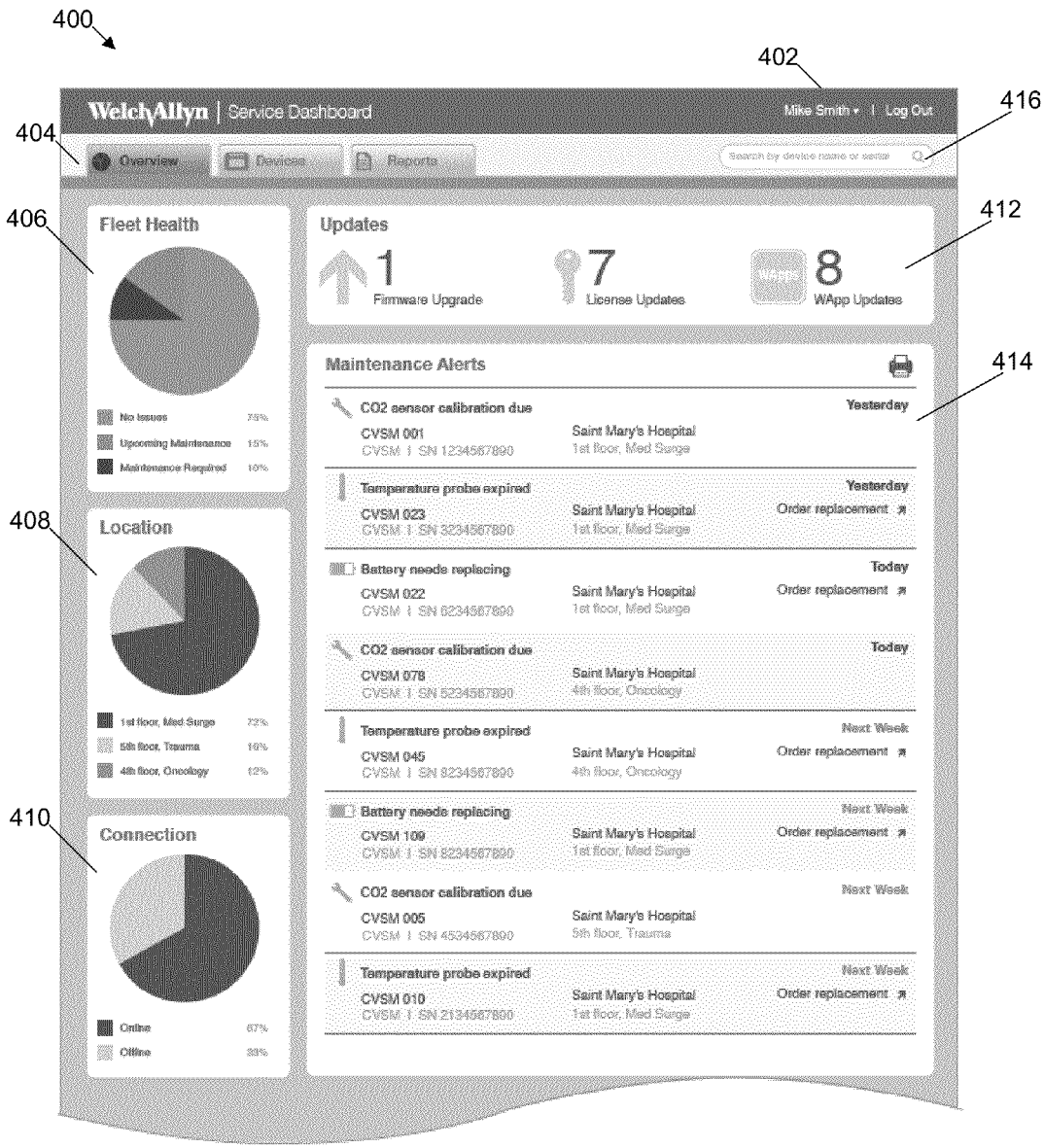
FIG. 4 shows an example user interface providing maintenance information for the medical devices of FIG. 1.

For example, referring now to FIG. 4, an example interface 400 for displaying information about medical devices is shown. In this example, the service device 114 accesses information on the server device 112 using a browser to obtain the information.

The example interface 400 includes authentication information 402, such as a user name and password that are provided by the technician to access the information. A tab structure 404 allows the technician to access various pages associated with the interface 400, including an overview page (FIG. 4), a devices page (FIGS. 5-11), and a reports page.

In example embodiments, the reports page provides access to various reporting features. Examples of such features include reports such as a calibration due date report and a preventive maintenance schedule report that list devices that are due for calibration or preventive maintenance, respectively. Other reports include reports that list the devices by usage (e.g., the top "x" device usage report) to help the user manage device supplies and/or to manage device aging. Other example reports include: reports by transactions per device, which lists the number of transactions at each device; utility reports to identify different financial means to purchase equipment, such as illustrating pay per use versus up-front capital costs; location of device reports that list devices by location; top error reports, which list the most common errors by device; wireless drop-out rates reports, which list wireless-related data per device; trend reports on usage of certain parameters to determine appropriate workflows and consistency to process (e.g., identification of re-takes of vitals that may lean towards requiring better training for staff); and reports listing software/firmware versions, license activations, and applications loaded per device.

The overview page provides a snapshot of an entire fleet of medical devices. In some examples, this could include the medical devices of a particular location (e.g., hospital or clinic), or multiple locations (e.g., a group of hospitals maintained by an entity).

A health module 406 provides a summary of the "health" of the medical devices. The health module 406 provides a graph showing the number of devices having no maintenance requirements, devices having upcoming maintenance requirements, and devices which currently require maintenance. In this example, the health information is shown in a graphical format.

A location module 408 provides a summary of the location of the medical devices. This can include a particular location within a facility (e.g., which floor, wing, etc.) or the location among a plurality of facilities (e.g., which hospital each device is located). In this example, the floors upon which the devices are located are shown in a graphical format.

A connection module 410 provides a summary of the connection state of the medical devices. This can include whether each medical devices is online (i.e., currently communicating with the server device 112) or offline (i.e., not currently communicating with the server device 112). This information is again provided in a graphical format.

The interface 400 also provides an update module 412 that summarizes the current state of the firmware and software on the medical devices. In this example, the update module 412 summarizes the number of devices needing firmware upgrade, license upgrades, and application upgrades. Other examples are possible.

The technician can use the information provided in the modules 406, 408, 410, 412 to make basic decisions about maintenance of the medical devices. For example, if the summaries indicate that a large number of medical devices will soon need maintenance, the technician may use this information to schedule additional technicians to handle the demand.

The interface 400 also includes a maintenance alert module 414 that provides more detail about the maintenance needs of each individual medical device. In this example, each medical device needing maintenance is listed, and the particular maintenance needs are detailed.

For example, the first entry indicates the location of a medical device "CVSM 0001," which is the first floor at Saint Mary's Hospital. The entry indicates the due date for the maintenance, which is "yesterday," and the particular maintenance needed is $CO_2$ sensor calibration. Other maintenance examples include temperature probe expiration (e.g., the probe expires after a given number of uses, such as 6000) and battery replacement.

For some maintenance needs, such as replacement of parts like temperature probes or batteries, links are provided so that the technician can easily access replacement parts. For example, the "Order replacement" link can be selected by the technician to access information about ordering replacement parts and/or actually placing an order for the parts.

As maintenance is performed on the devices, the devices report back to the server device 112 with updated maintenance information. This updated maintenance information impacts the information that is displayed to the technician on the interface 400. For example, if the CVSM 001 $CO_2$ sensor is calibrated, the CVSM 001 will report that the maintenance has been performed the next time the CVSM 001 communicates with the server device 112. The interface 400 can thereupon be updated by, for example, removing the entry for the CVSM 001 from the maintenance alert module 414. Manual removal of entries is also possible.

If a particular device must be located, a search box 416 can be used. For example, the technician can put a device's name (e.g., CVSM 001) or serial number (e.g., 1234567890) into the search box 416 to access information about the device, as described further below.

Figure 5:
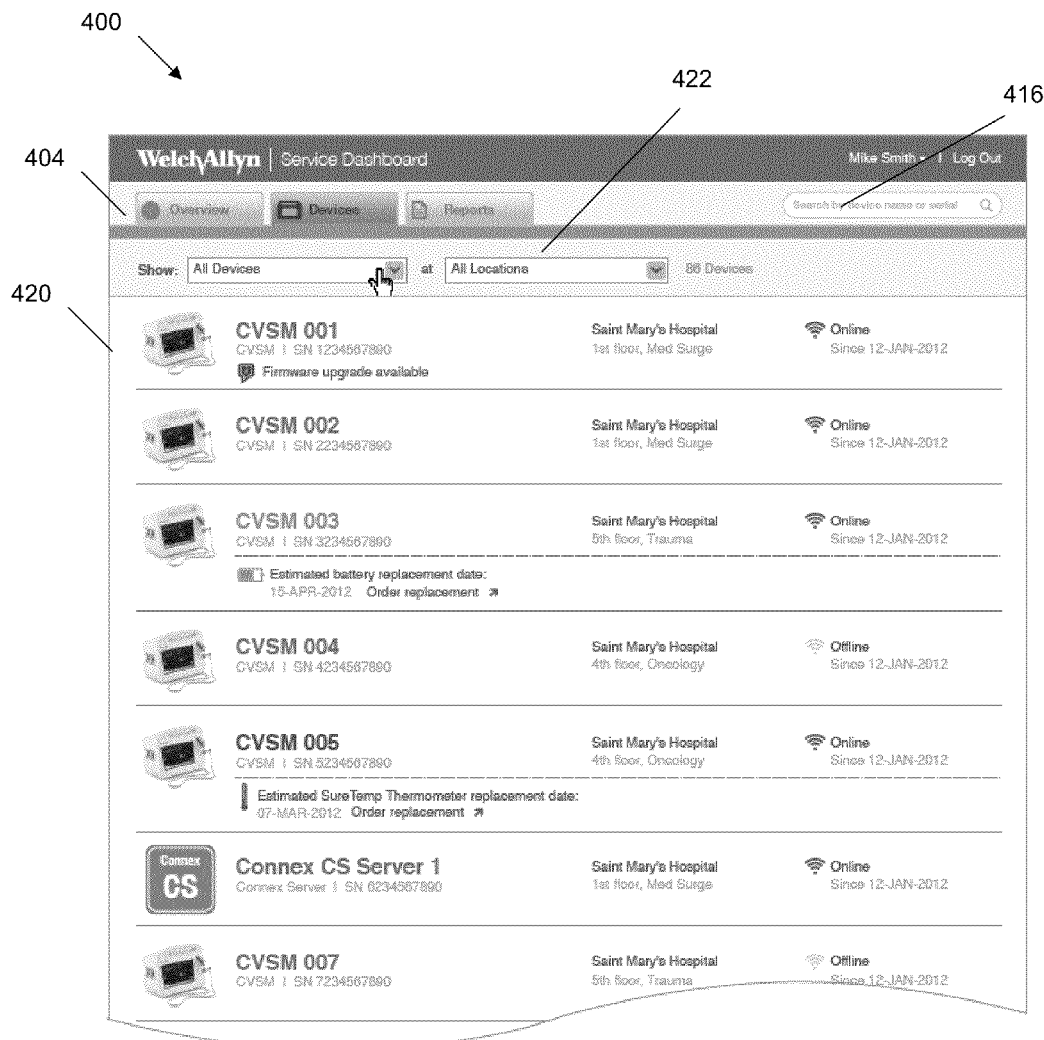
FIG. 5 shows another view of the user interface of FIG. 4.

Referring now to FIG. 5, a devices page 420 is shown on the interface 400 when selected on the tab structure 404. The devices page 420 provides more detailed information about each of the medical devices.

In this example, the devices page 420 provides each device's name, serial number, location, and connection state (e.g., online or offline, and duration for the current state). In addition, any maintenance requirements are listed for each medical device. For example, for the CVSM 001, a firmware upgrade is available, and for the CVSM 003, a battery is estimated to be needed to be replaced on Apr. 15, 2012. A link to order replacement parts is provided. In another example, the CVSM 005 requires a thermometer replacement.

The devices page 420 also provides a filter pane 422 that allows the technician to filter the devices that are shown. In this example, the filter pane 422 allows for filtering by device type and/or location.

Figure 6:
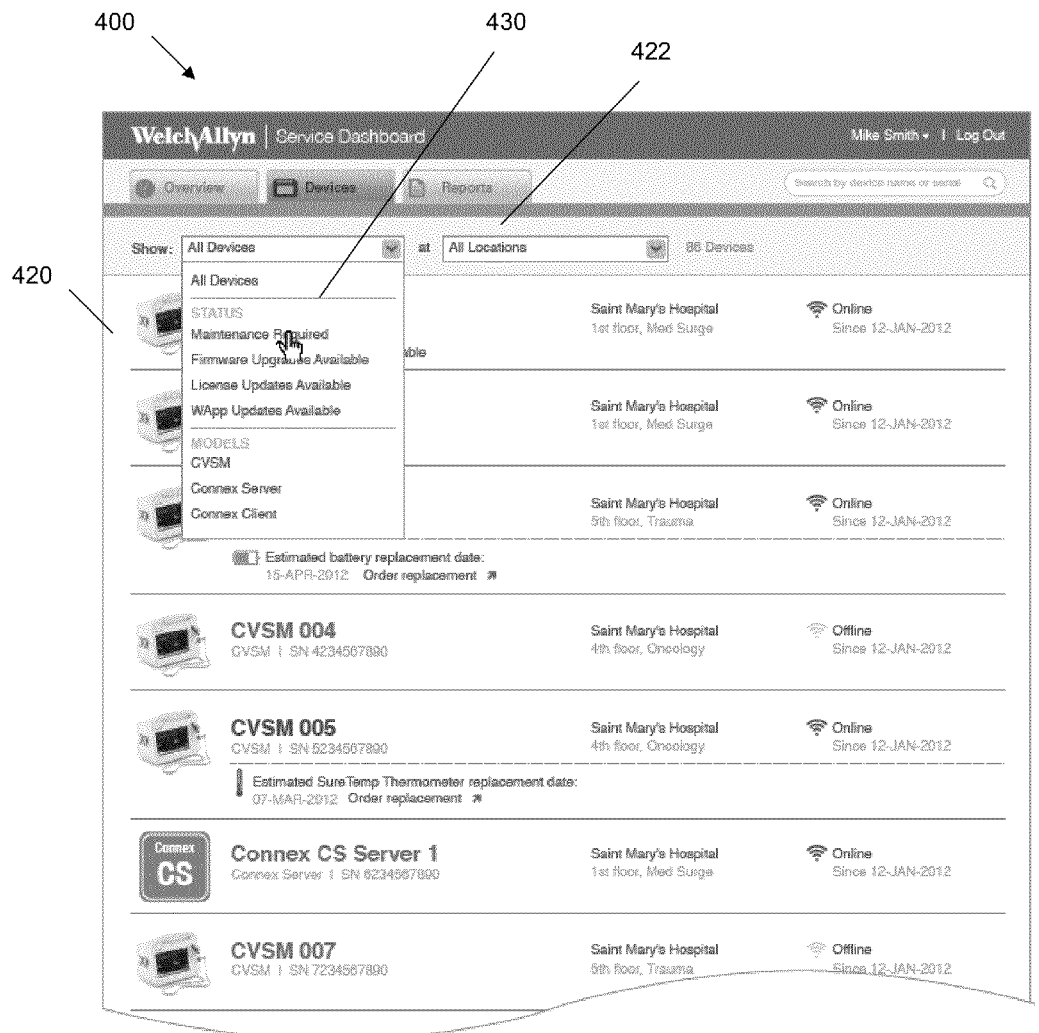
FIG. 6 shows another view of the user interface of FIG. 4.

As shown in FIG. 6, if device type is selected on the filter pane 422, a dropdown 430 is provided that allows the user to filter the devices that are shown on the devices page 420 by specific parameters, such as: maintenance required (e.g., maintenance, firmware upgrade, license update, or application update); or model type for the medical device.

Figure 7:
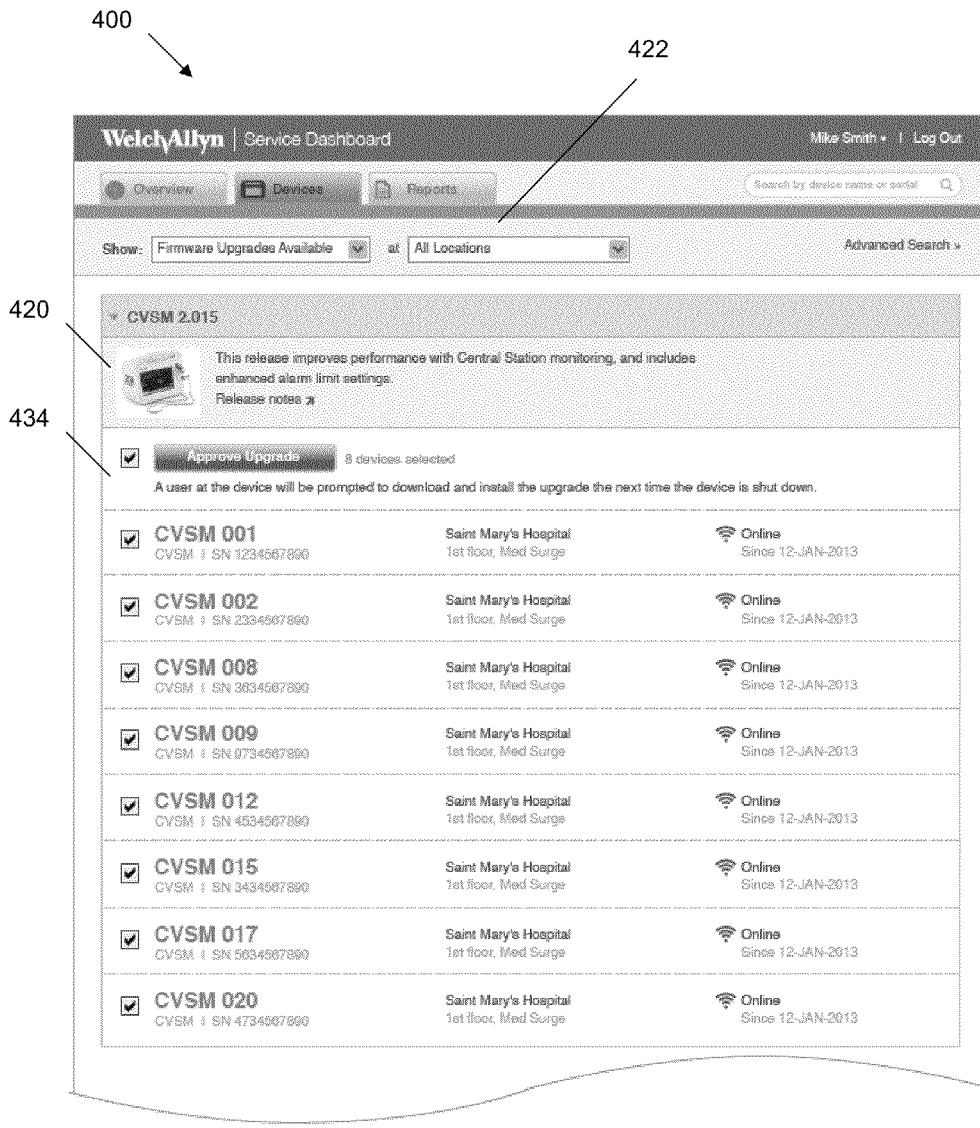
FIG. 7 shows another view of the user interface of FIG. 4.

Referring to FIG. 7, if a selection is made on the dropdown, such as "Firmware Upgrade Available," the devices page 420 is modified to list those devices needing firmware upgrades. In this example, details about the firmware upgrade are provided, along with a list of those devices that need the upgrade.

In addition, a firmware upgrade module 434 is provided that allows the technician to select which devices to upgrade. For example, a checkbox is associated with each device listed, and the technician can select the checkboxes associated with the desired devices to upgrade. Upon selection, the "Approve Upgrade" button is selected to schedule the selected medical devices for firmware upgrades. As described further below, each of the selected devices will download the noted firmware and prompt the user for installation at the next reboot of the device.

Referring again to FIG. 5, the filter pane 422 provides similar functionality if the location is selected, including a dropdown that allows the technician to filter the devices shown on the devices page 420 based on the location of the devices (e.g., at certain facilities and/or at certain locations within a facility).

Figure 8:
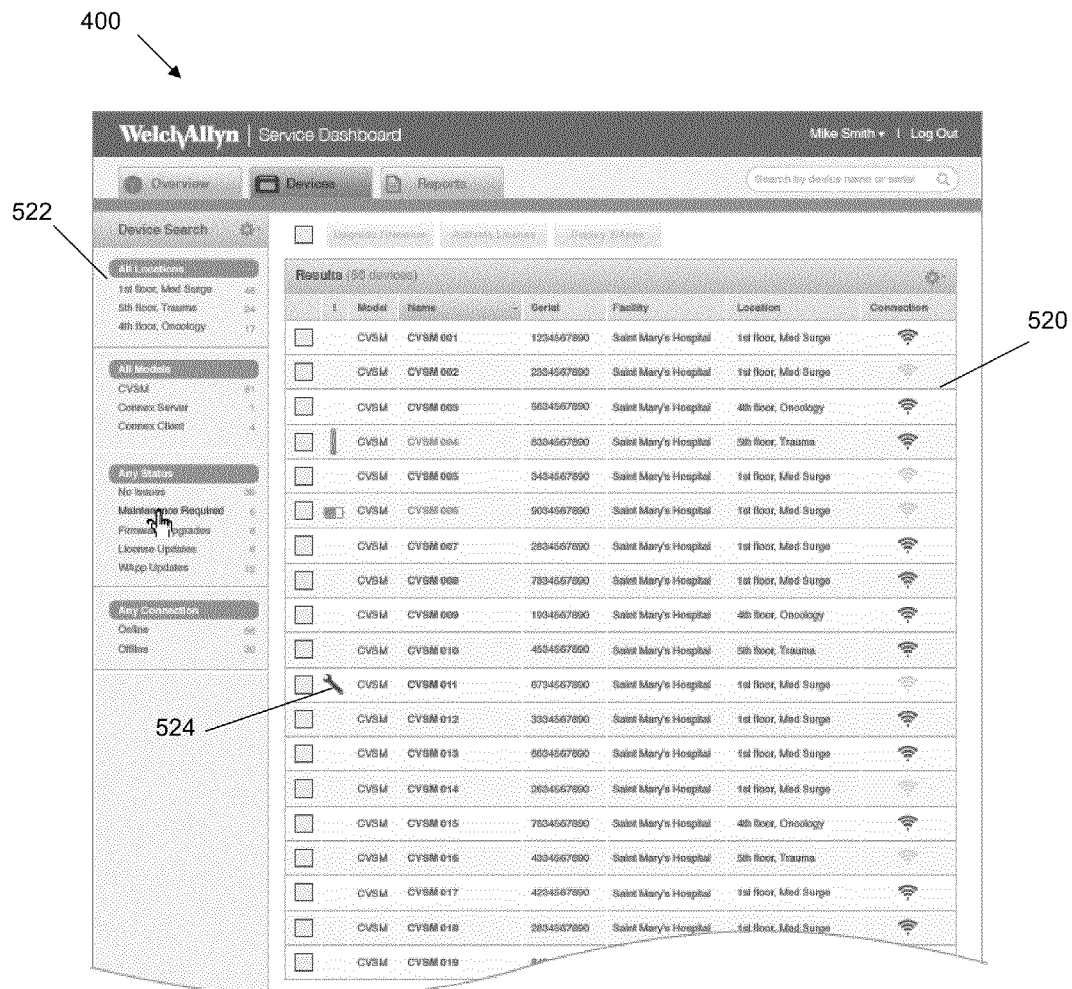
FIG. 8 shows another view of the user interface of FIG. 4.

Referring to FIG. 8, another example of a devices page 520 is shown on the interface 400. The devices page 520 is similar to that of the devices page 420, except the data associated with each medical device is shown in a tabular, summary format. Icons are provided to indicate a type of maintenance required for certain devices, such as an icon 524 that indicates general maintenance is needed. This allows for device information to be shown in a more compact format.

In addition, a modified filter pane 522 is provided that allows the user to filter the device shown based on location, model type, maintenance status, and/or connection state.

Figure 9:
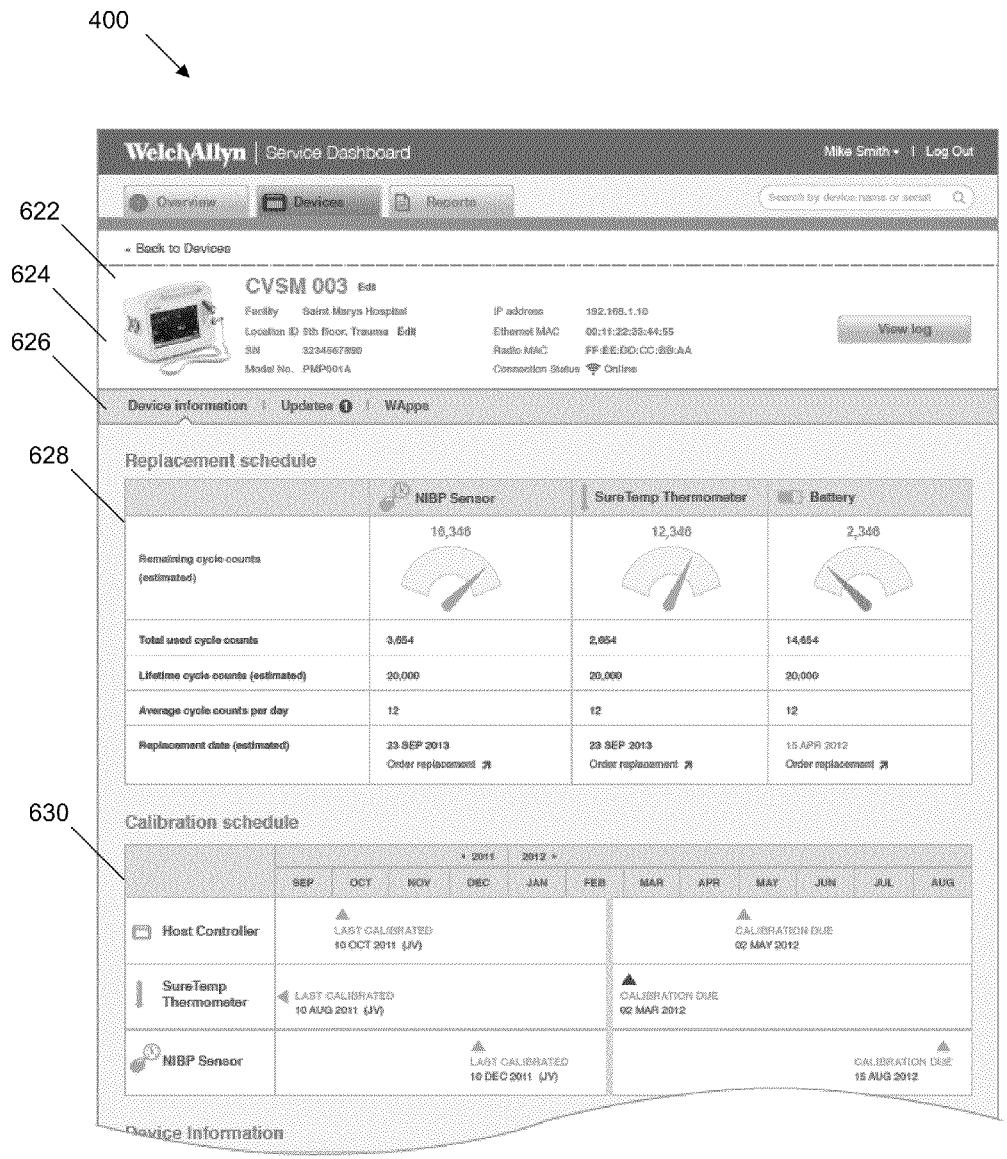
FIG. 9 shows another view of the user interface of FIG. 4.
Figure 10:
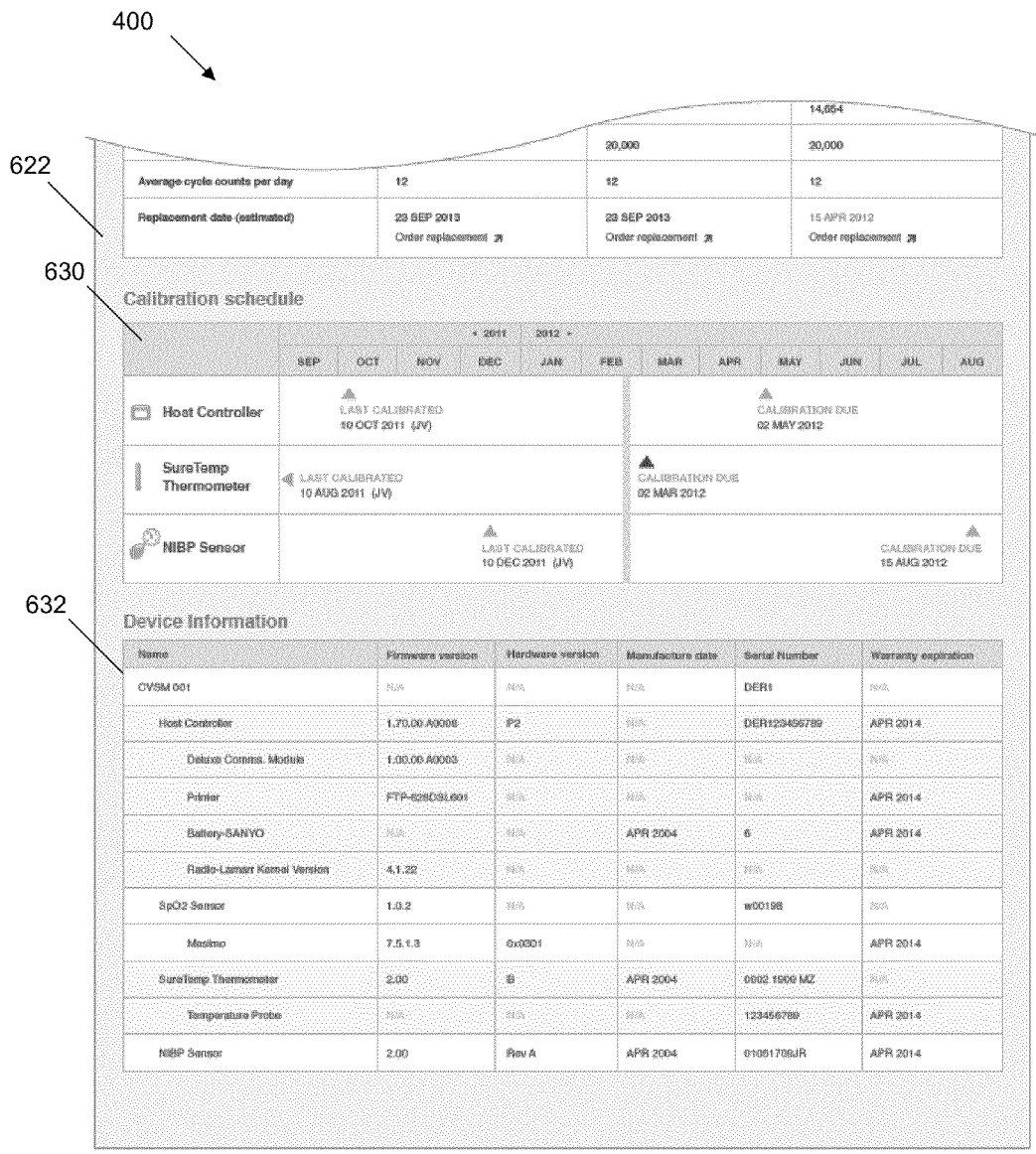
FIG. 10 shows another view of the user interface of FIG. 4.

Referring now to FIGS. 9-10, additional details about a specific medical device are provided on a device details page 622 when a device is selected from the interface 400, such as from the devices pages 420, 520.

In this example, the device details page 622 includes a device summary module 624 providing the information about the device, such as device name, location, serial number, model number, IP address, Ethernet and Radio MAC addresses, and connection state. Log files associated with the medical device can be accessed, and information associated with the device (e.g., device name) can be edited.

In addition, the device details page 622 provides a tab structure 626 that allows the technician to select between device information (FIGS. 9-10), updates (FIG. 11), or applications.

With the device information selected, a replacement schedule module 628 is provided. This module 628 provides information about the components that need to be replaced on the medical device. In the example, the components include an NIBP sensor, a thermometer, and a battery. The module 628 provides information about the cycle counts, expected life, average usage (e.g., per day), and estimated replacement date Links to access replacement parts are also provided.

A calibration module 630 on the device details page 622 provides information about the calibration of the medical device. This includes the components needing calibration (e.g., host controller, thermometer, and NIBP sensor), as well as a schedule of when the last calibration was performed, and the next calibration is due. In this example, the schedule is displayed as a timeline that allows the technician to easily conceptualize maintenance needs over time.

A device information module 632 provides detailed information about various aspects of the components of the device. This information can include firmware versions, hardware versions, manufacture dates, serial numbers, and warranty expirations. Other configurations are possible.

Figure 11:
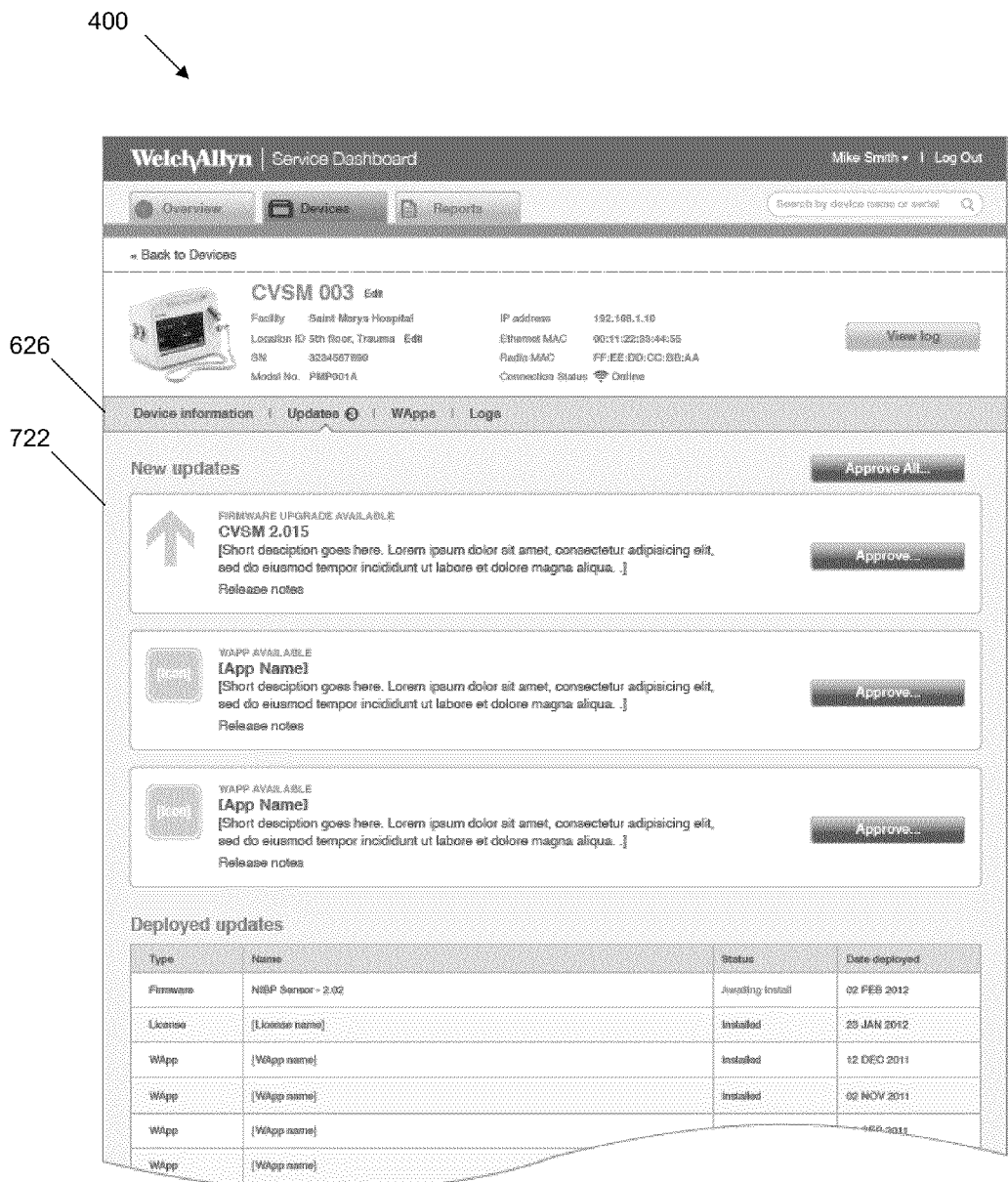
FIG. 11 shows another view of the user interface of FIG. 4.

Referring now to FIG. 11, when updates are selected on the tab structure 626, an updates page 722 is provided that lists the new updates that are available for the medical device. The technician can review information about each update and access additional information about the updates (i.e., release notes). In addition, the technician can approve the updates separately or altogether. As described further below, the device will download the selected update(s) and prompt the user for installation at the next reboot of the device. In addition, information about the deployed updates (both awaiting install and installed) is provided.

Figure 12:
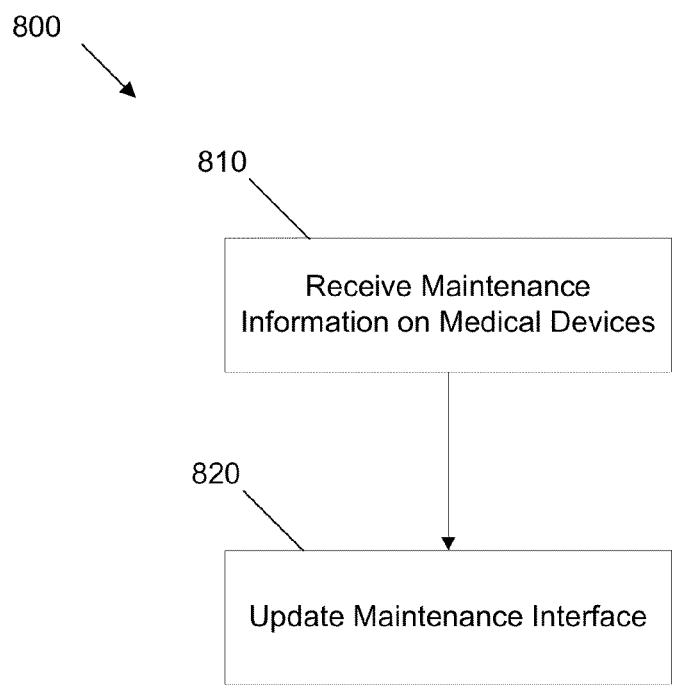
FIG. 12 shows an example method for maintaining medical devices.

Referring now to FIG. 12, an example method 800 for providing maintenance information for medical devices is shown.

At operation 810, information about the maintenance requirements of the medical devices is received. Such information can include maintenance needed for particular components associated with the medical devices and/or upgrades to firmware and/or software on the medical devices.

Next, at operation 820, the maintenance interface is updated based on the information received. This includes indicating that additional maintenance is needed and providing an indication that maintenance has been performed by, for example, removing the medical device from the entry indicating that maintenance is needed.

Figure 13:
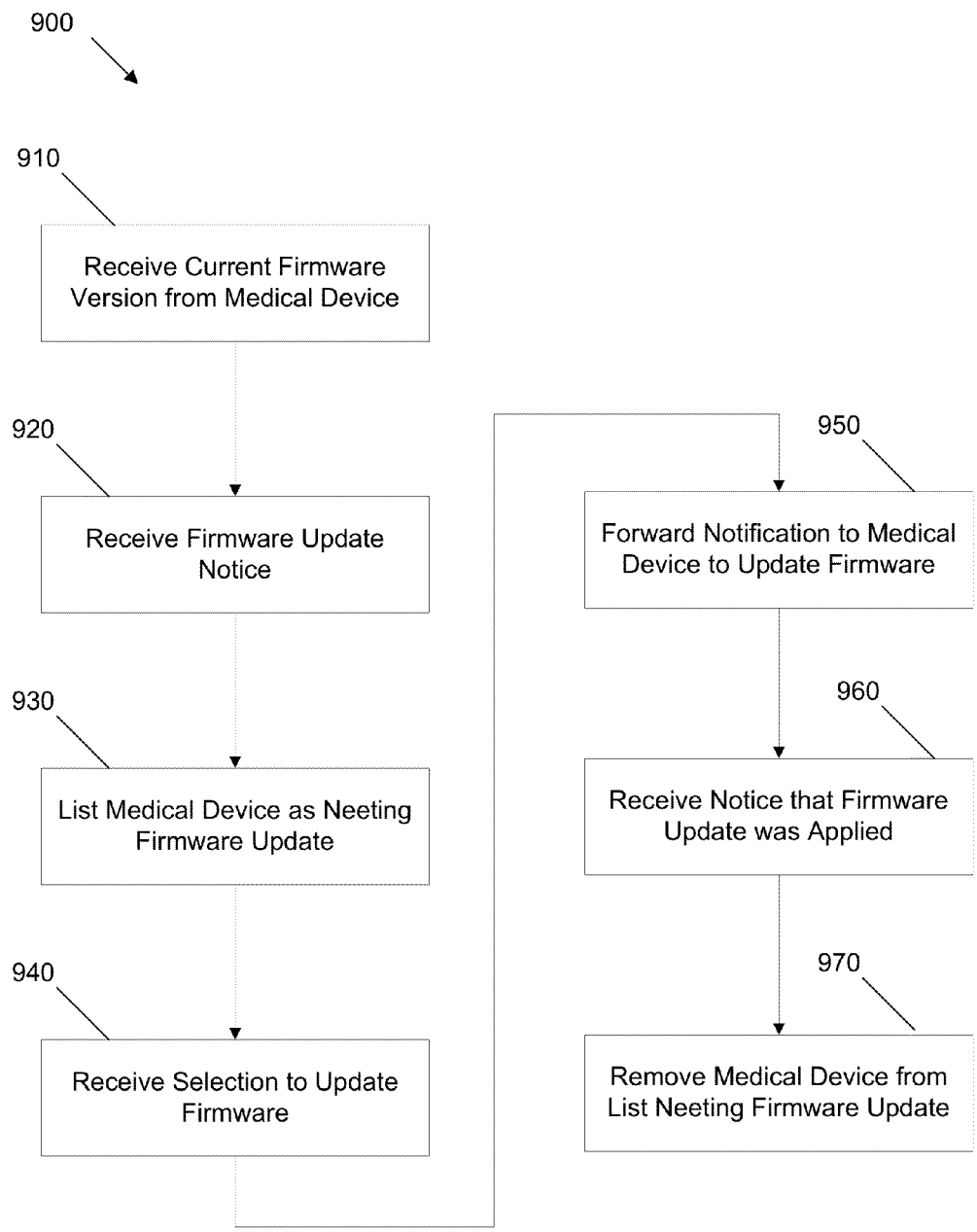
FIG. 13 shows another example method for maintaining medical devices.

One example of such a method is provided in FIG. 13. In this example method 900, the firmware for a medical device is updated.

Initially, at operation 910, the server device receives the current firmware information (e.g., version) for a medical device. Next, at operation 920, the server device receives notification that a firmware update is available for the medical device.

At operation 930, the medical device is listed as needing a firmware update. At operation 940, confirmation is provided to the server device to apply the firmware update.

Next, at operation 950, the server device notifies the medical device to update the firmware. This notification is typically provided the next time the medical device connects to the server device or an intermediate device communicating therewith.

Upon notification, the medical device downloads the firmware. When the medical device next reboots, a prompt is provided to the user of the medical device requesting permission to apply the firmware update. Once applied, the medical device reports the update back to the server device.

At operation 960, the server device receives notification that the firmware update was applied. Finally, at operation 970, the medical device is removed from the list of devices needing firmware updates.

Figure 14:
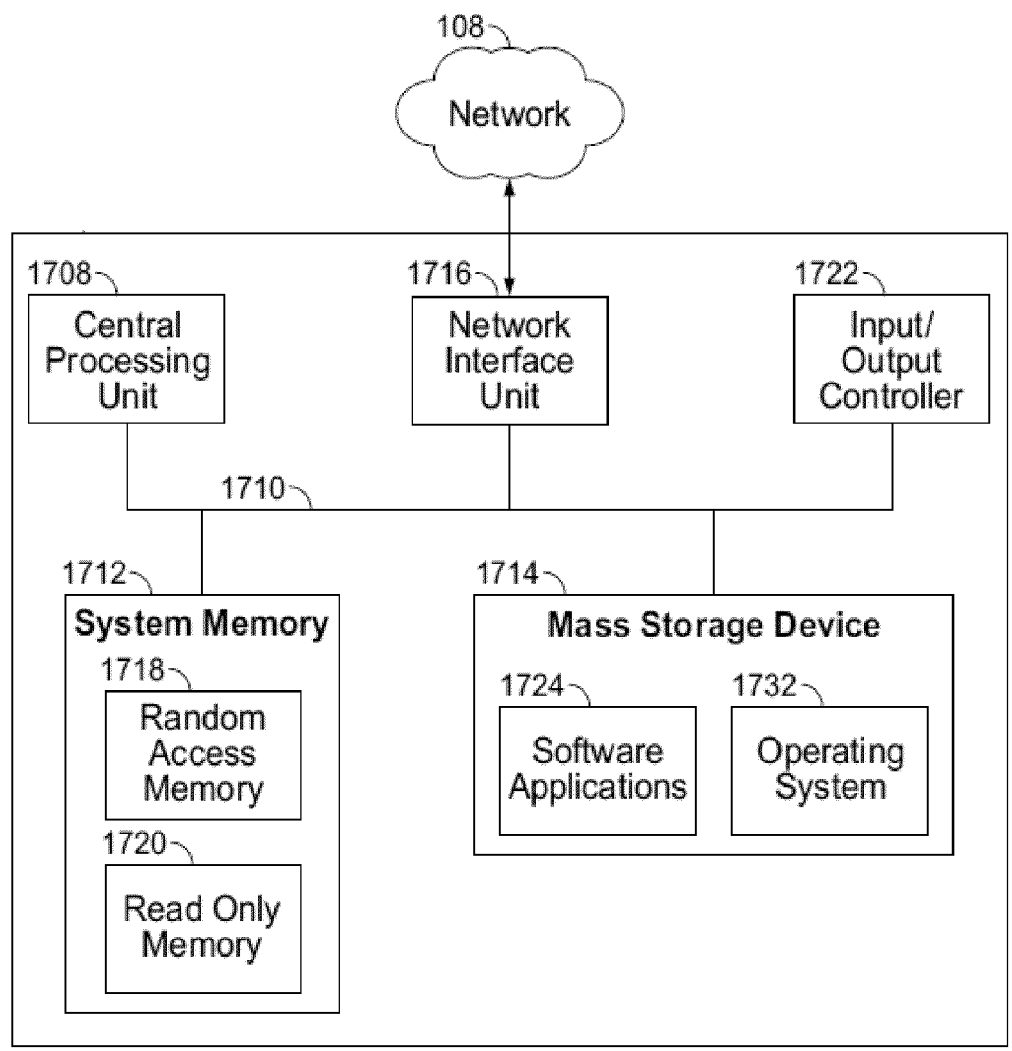
FIG. 14 shows example components of a medical device of the system of FIG. 1.

FIG. 14 illustrates example physical components of a computing device, such as the devices 102, 104, 112, 114. As illustrated, the device includes at least one central processing unit ("CPU") 1708, a system memory 1712, and a system bus 1710 that couples the system memory 1712 to the CPU 1708. The system memory 1712 includes a random access memory ("RAM") 1718 and a read-only memory ("ROM") 1720. A basic input/output system containing the basic routines that help to transfer information between elements within the device, such as during startup, is stored in the ROM 1720. The device further includes a mass storage device 1714. The mass storage device 1714 is able to store software instructions and data.

The mass storage device 1714 is connected to the CPU 1708 through a mass storage controller (not shown) connected to the bus 1710. The mass storage device 1714 and its associated computer-readable data storage media provide non-volatile, non-transitory storage for the device. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the device.

According to various embodiments of the invention, the device may operate in a networked environment using logical connections to remote network devices through the network 108, such as a local network, the Internet, or another type of network. The device connects to the network 108 through a network interface unit 1716 connected to the bus 1710. The network interface unit 1716 may also be utilized to connect to other types of networks and remote computing systems. The device also includes an input/output controller 1722 for receiving and processing input from a number of other devices, including a keyboard, a mouse, a touch user interface display screen, or another type of input device. Similarly, the input/output controller 1722 may provide output to a touch user interface display screen, a printer, or other type of output device.

As mentioned above, the mass storage device 1714 and the RAM 1718 of the device can store software instructions and data. The software instructions include an operating system 1732 suitable for controlling the operation of the device. The mass storage device 1714 and/or the RAM 1718 also store software instructions, that when executed by the CPU 1708, cause the device to provide the functionality of the device discussed in this document. For example, the mass storage device 1714 and/or the RAM 1718 can store software instructions that, when executed by the CPU 1708, cause the physiological monitor device to display the home screen 600 and other screens.

Although the example medical devices described herein are devices used to monitor patients, other types of medical devices can also be used. For example, the different components of the CONNEX™ system, such as the intermediary servers that communication with the monitoring devices, can also require maintenance in the form of firmware and software updates. These intermediary servers can be managed by the systems and methods described herein to update the maintenance requirements of the servers.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A method for providing maintenance information for a plurality of medical devices, the method comprising:
    receiving maintenance information from the medical devices;
    providing an interface including a summary of the maintenance information, the summary including:
        a summary of a maintenance status of the medical devices;
        a summary of a location of the medical devices, the location including a facility and a floor;
        a summary of a state of connection of the medical devices, the state of connection indicating whether each medical device is currently communicating with a server and a duration for the current state; and
        a list of the medical devices needing maintenance, the list including a type of maintenance needed for each of the medical devices in the list and an icon indicating the type of maintenance;
    providing access to the summary of the maintenance information outside a network associated with the medical devices;
    providing a replacement schedule, including an estimated replacement date, cycle counts, expected life, and average usage;
    providing information about replacement of components associated with one of the medical devices;
    providing information about calibration of components associated with one of the medical devices;
    receiving an indication that maintenance for a given medical device has been performed;
    removing the given medical device from the list; and
    providing a wireless report including a list of wireless-related data per device, the wireless report including wireless drop-out rates for one or more of the medical devices.

2. The method of claim 1, wherein the summary further includes a summary of a state of connection of the medical devices.

3. The method of claim 1, the summary further includes a summary of available firmware and software upgrades for the medical devices.

4. The method of claim 3, further comprising allowing a user to approve the firmware or software upgrade to be applied one or more of the medical devices on the list.

5. The method of claim 4, further comprising notifying the medical devices to upgrade the firmware or software.

6. The method of claim 1, further comprising filtering the list of the medical devices based on a device type or a location.

7. The method of claim 1, wherein the type of maintenance needed includes replacement of components associated with the medical devices, and upgrade of firmware or software of the medical devices.

8. A non-transitory computer-readable storage medium encoding instructions that, when executed by a processor, cause the processor to perform steps comprising:
    receiving maintenance information from the medical devices;
    providing a summary of the maintenance information, the summary including:
        a summary of a maintenance status of the medical devices;
        a summary of a location of the medical devices, the location including a facility and a floor;
        a list of the medical devices needing maintenance, the list including a type of maintenance needed for each of the medical devices in the list;
        a summary of a state of connection of the medical devices, the state of connection indicating whether each medical device is currently communicating with a server and a duration for the current state;
        a replacement module comprising a replacement schedule, an estimated replacement date, cycle counts, expected life, and average usage; and
        a summary of firmware and software updates for the medical devices;
    filtering the list of the medical devices based on device or location;
    allowing a user to approve the firmware or software upgrade to be applied one or more of the medical devices on the list;
    notifying the medical devices to update the firmware or software;
    providing information about replacement of components associated with one of the medical devices;

providing information about calibration of components associated with one of the medical devices;
receiving an indication that maintenance for a given medical device has been performed;
removing the given medical device from the list; and
providing a wireless report including a list of wireless-related data for one or more medical devices, the wireless report including wireless drop-out rates for one or more of the medical devices.

\* \* \* \* \*